(12) United States Patent
O'Day (10) Patent No.: US 8,932,270 B2
(45) Date of Patent: Jan. 13, 2015

(54) VARIABLE INFUSION LENGTH CATHETER AND METHOD

(71) Applicant: Cook Medical Technologies LLC, Bloomington, IN (US)

(72) Inventor: Therese J. O'Day, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 72 days.

(21) Appl. No.: 13/761,280

(22) Filed: Feb. 7, 2013

(65) Prior Publication Data

US 2013/0274711 A1    Oct. 17, 2013

Related U.S. Application Data

(60) Provisional application No. 61/622,585, filed on Apr. 11, 2012.

(51) Int. Cl.
| | | |
|---|---|---|
| *A61M 5/14* | (2006.01) | |
| *A61M 31/00* | (2006.01) | |
| *A61M 25/00* | (2006.01) | |
| *A61M 5/168* | (2006.01) | |
| *A61M 39/08* | (2006.01) | |

(52) U.S. Cl.
CPC ........... *A61M 5/16813* (2013.01); *A61M 25/00* (2013.01); *A61M 39/08* (2013.01)
USPC ............................ 604/256; 604/523; 604/508

(58) Field of Classification Search
CPC ................... A61M 25/007; A61M 2025/0057; A61M 2025/0079; A61M 2025/0004; A61M 2025/0039
USPC ........................... 604/256, 264, 523, 527, 508
See application file for complete search history.

(56) References Cited

U.S. PATENT DOCUMENTS

| | | |
|---|---|---|
| 4,968,306 A | 11/1990 | Huss et al. |
| 5,425,723 A | 6/1995 | Wang |
| 5,569,215 A | 10/1996 | Crocker |
| 6,044,845 A * | 4/2000 | Lewis ........................ 128/898 |
| 6,575,932 B1 | 6/2003 | O'Brien et al. |
| 2006/0229573 A1 | 10/2006 | Lamborne |

* cited by examiner

*Primary Examiner* — Rebecca E Eisenberg
(74) *Attorney, Agent, or Firm* — Liell & McNeil (57) ABSTRACT

A variable infusion length catheter includes a tube assembly having a plurality of coaxial tubes each with a plurality of side ports formed therein, and having among the tubes a plurality of different rotational configurations each defining a different pattern of fluid communication among the side ports and a corresponding different infusion length of the catheter. Related methodology is also disclosed.

20 Claims, 5 Drawing Sheets

VARIABLE INFUSION LENGTH CATHETER AND METHOD

RELATION TO OTHER PATENT APPLICATION

This application claims priority to provisional patent application 61/622,585, filed Apr. 11, 2012 with the same title.

TECHNICAL FIELD

The present disclosure relates generally to infusion catheters, and more particularly to adjusting an infusion length of an infusion catheter via changing a pattern of fluid communication among side ports in a tube assembly thereof.

BACKGROUND

Percutaneous access to the cardiovascular system is used to diagnose, evaluate, and treat a variety of conditions. A typical procedure involves passing a wire guide through an opening in a patient's skin, often by way of an introducer sheath, which connects to a vascular structure such as a vein or artery. The wire guide can then be passed through the cardiovascular system to a location of interest within the patient. Once the wire guide has been appropriately positioned, a catheter may be passed into the patient and guided by the wire guide to a location where a procedure is to be performed. Angioplasty, imaging, and the placement of stents, grafts, filters and other devices, are common procedures which are performed according to variations of the above general technique. It is also common to use percutaneous access for the placement of catheters which deliver fluid at an intraluminal treatment site. Devices known as infusion catheters are used to deliver a therapeutic treatment fluid such as a thrombolytic agent to a clot or the like within a vein or artery.

A wide variety of infusion catheter designs are known and commercially available. One general class of infusion catheters utilizes a longitudinally extending lumen which connects a supply of therapeutic fluid located outside of the patient with an intraluminal space by way of ports communicating between the lumen and the intraluminal space. In such infusion catheters, the infusion fluid is typically delivered from infusion ports placed in proximity to the area to be treated. Since a distribution of the infusion ports in the catheter may often be different from the length of the treatment area, designs have been proposed in which a clinician can adjust which of the infusion ports are presently available for infusing the fluid, such as covering some of the infusion ports with a sheath, or sliding the sheath to expose previously covered infusion ports. One such design is known from U.S. Pat. No. 6,575,932 to O'Brien et al. O'Brien proposes a multi-balloon local delivery device, which purportedly allows precise adjustment of an inter-balloon distance to permit controlled delivery of therapeutics to a discreet length of a hollow tubular organ wall. While O'Brien and other slide type infusion catheter designs may function adequately, sliding components of a catheter within a treatment area from a location outside of the patient can be cumbersome, and in some instances risks introducing contaminated parts of the device into the patient. In other words, a slidable sheath strategy can require a user to position a device within a patient, slide part of it out of the patient, and then potentially slide a non-sterile part back into the patient. Alternatively, the clinician might simply be prevented from proceeding in an optimum way.

SUMMARY OF THE DISCLOSURE

In one aspect, a variable infusion length catheter includes a tube assembly having a distal end positionable within a body lumen in a patient, and a proximal end including a fitting with an inlet orifice formed therein, for fluidly connecting with a supply of liquid. The tube assembly further includes an outer tube defining a longitudinal axis and having formed therein a plurality of axially spaced outer side ports, for infusing the liquid into the body lumen. The tube assembly further includes at least one inner tube positioned coaxially within the outer tube, and having formed therein a supply passage configured to receive the liquid from the inlet orifice, and a plurality of axially spaced inner side ports configured to convey the liquid from the supply passage to the outer side ports. The at least one inner tube is rotatable within the outer tube to change a pattern of fluid communication among the outer and inner side ports and responsively adjust the infusion length of the catheter.

In another aspect, a method of percutaneously treating a patient includes conveying a liquid from a plurality of inner side ports formed in an inner tube of a coaxial tube assembly in an infusion catheter to a plurality of outer side ports formed in an outer tube of the coaxial tube assembly, and infusing the liquid from the outer side ports into a body lumen of the patient. The method further includes rotating the inner tube to change a pattern of fluid communication among the outer and inner side ports which defines an infusion length of the infusion catheter, and infusing additional liquid into the body lumen at an adjusted infusion length defined by the changed pattern of fluid communication.

In still another aspect, a tube assembly for an infusion catheter includes an outer tube defining a longitudinal axis and having formed therein a plurality of axially spaced outer side ports, for infusing a liquid into a body lumen of a patient. The tube assembly further includes at least one inner tube positioned coaxially within the outer tube, and having formed therein a supply passage configured to receive the liquid from an inlet orifice of the infusion catheter, and a plurality of axially spaced inner side ports configured to fluidly connect the outer side ports with the supply passage. The at least one inner tube is rotatable within the outer tube to adjust the tube assembly from a first rotational configuration where only some of the outer side ports are in fluid communication with the supply passage and the catheter has a partial infusion length, to a second rotational configuration where all of the outer side ports are in fluid communication with the supply passage and the catheter has a full infusion length.

DETAILED DESCRIPTION

Figure 1:
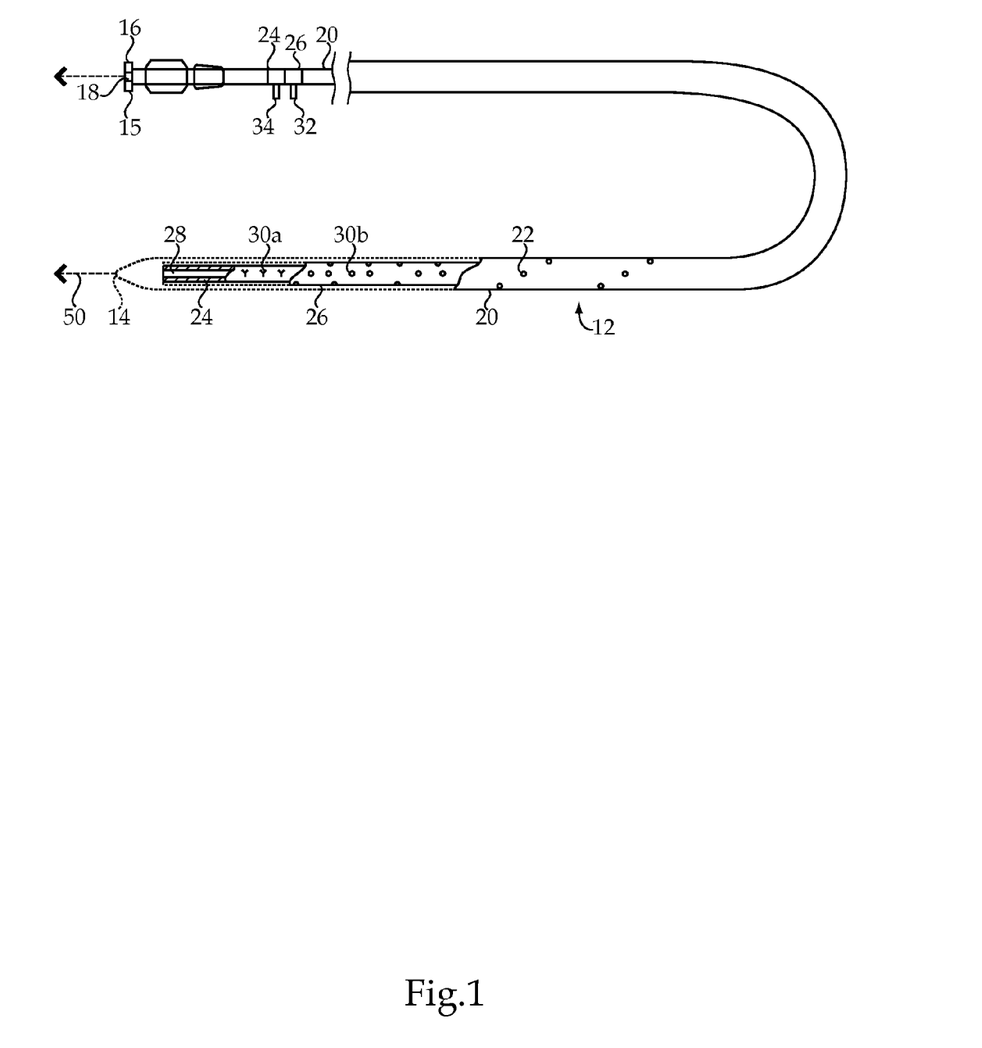
FIG. 1 is a side diagrammatic view of a variable infusion length catheter, according to one embodiment.

Referring to FIG. 1, there is shown a variable infusion length catheter 10 according to one embodiment. Catheter 10 may include a tube assembly 12 having a distal end 14 positionable within a body lumen in a patient, and a proximal end 15 having a fitting 16. Fitting 16 may include a luer fitting or the like having an inlet orifice 18 formed therein, for fluidly connecting with a supply of liquid. Tube assembly 12 may include an outer tube 20 defining a longitudinal axis 50, and having formed therein a plurality of axially spaced outer side ports 22, for infusing the liquid into the body lumen. Tube assembly 20 may also include at least one inner tube, and in the illustrated case a first inner tube 24 and a second inner tube 26, positioned coaxially within outer tube 20. First inner tube 24 may have formed therein a supply passage 28 configured to receive the liquid from inlet orifice 18, and a plurality of axially spaced inner side ports 30a configured to convey the liquid from supply passage 28 to outer side ports 22. In a practical implementation strategy, second inner tube 26 is positioned radially between first inner tube 24 and outer tube 20, and has another plurality of axially spaced inner side ports 30b formed therein, and configured to convey the liquid from inner side ports 30a to outer side ports 22. The one or more inner tubes 24 and 26 may be rotatable within outer tube 20, and rotatable relative to one another, to change a pattern of fluid communication among outer side ports 22 and inner side ports 24 and 26, and responsively adjust the infusion length of catheter 10. In one embodiment, first inner tube 24 may have an outer diameter dimension of about 5 French, second inner tube 26 may have an outer diameter dimension of about 6 French, and outer tube 20 may have an outer diameter dimension of about 7 French, although the present disclosure is not thusly limited.

FIG. 1 illustrates catheter 10 in partial cutaway, to illustrate inner tubes 24 and 26 and their respective sets of inner side ports 30a and 30b. A handle or analogous device 32 is coupled with inner tube 26 to enable a clinician to rotate inner tube 26 relative to one or both of inner tube 24 and outer tube 20 to change the pattern of fluid communication mentioned above. Another handle 34 may be coupled with inner tube 24 to enable a clinician to rotate inner tube 24 relative to one or both of outer tube 20 and inner tube 26 for analogous purposes. In a practical implementation strategy, outer side ports 22 have at least three different combinations of radial alignment with inner side ports 30a and 30b, the combinations of radial alignment enabling a user to selectively place all or less than all of outer side ports 22 in fluid communication with passage 28 via inner side ports 30a and 30b. Based upon the at least three different combinations of radial alignment, and corresponding at least three different patterns of fluid communication, catheter 10 may have at least three different available infusion lengths. In certain embodiments, catheter 10 may have six different available infusion lengths, or potentially even more. As used herein, the term "infusion length" refers not to an absolute length of catheter 10 which is available for infusion, but to which part of the total potential infusion length of catheter 10 is presently available for infusion.

As will be further apparent by way of subsequent description and illustrations, catheter 10 may have a full infusion length where all of outer side ports 20 are in fluid communication with supply passage 28, a proximal infusion length where only a proximal group of outer side ports 22 are in fluid communication with passage 28, a distal infusion length where only a distal group of outer side ports 22 are in fluid communication with passage 28, and a middle infusion length where only a middle group of outer side ports 22 are in fluid communication with passage 28. Catheter 10 may also have a combined proximal and middle infusion length where both proximal and middle, but not distal, groups of outer side ports 28 are in fluid communication with passage 28, and a combined distal and middle infusion length where distal and middle, but not proximal, groups of outer side ports 22 are in fluid communication with passage 28. Changing the combination of radial alignment among outer side ports 22 and inner side ports 30a and 30b can thus enable a clinician to set catheter 10 at different rotational configurations among tubes 24, 26 and 20, to selectively infuse liquid from only a desired part of catheter 10 and towards only targeted locations within a patient's anatomy.

These capabilities arise at least in part from the arrangements of the various outer and inner side ports contemplated herein, within the corresponding tube. In a practical implementation strategy, outer side ports 22 may have a uniform density in an axial direction, meaning that outer side ports 22 are uniformly distributed in an axial direction along outer tube 20. Outer side ports 22 may also circumferentially advance about outer tube 20, and in a practical implementation strategy may be arranged in a spiral pattern. Outer side ports 22 may further be normally open.

Some of inner side ports 30a and 30b may respectively be arranged in a spiral pattern that matches the spiral pattern of outer side ports 22. Each of inner side ports 30a and 30b may also include multiple side ports at certain axial locations, facilitating radial alignment with corresponding ones of outer side ports 22 when tube 24 or tube 26 is rotated, in a manner that will be apparent from the following description. A number of inner side ports 30a and a number of inner side ports 30b may be equal in certain embodiments. A number of outer side ports 22 may be a lesser number than the number of inner side ports 30a and 30b.

As noted above, an arrangement of outer side ports 22 and inner side ports 30a and 30b may be used to impart the different combinations of radial alignment and different available infusion lengths. To this end, inner side ports 30a and inner side ports 30b may define opposite density gradients in an axial direction. This feature may be understood to mean that inner tube 24 may have more of its side ports 30a in a distal section versus a proximal section, while inner tube 26 may have more of its side ports 30b in a proximal section versus a distal section. These patterns might also be reversed, with inner tube 24 having more proximal side ports and fewer distal, and inner tube 26 having more distal side ports and fewer proximal. In a practical implementation strategy, inner side ports 30a and inner side ports 30b may have equal densities in a middle section, such as a middle one-third of the corresponding tube 24 and 26. These features too will be further apparent from the following description Inner side ports 30b may be normally open, whereas inner side ports 30a may be normally closed. This means that in at least certain embodiments, some fluid pressure in passage 28 may be required to urge inner side ports 30a to a fully open state. This feature has been observed to enable relatively uniform distribution of infusion liquid along whatever infusion length of catheter 10 is presently selected, and particularly where a full infusion length is used.

Figure 2:
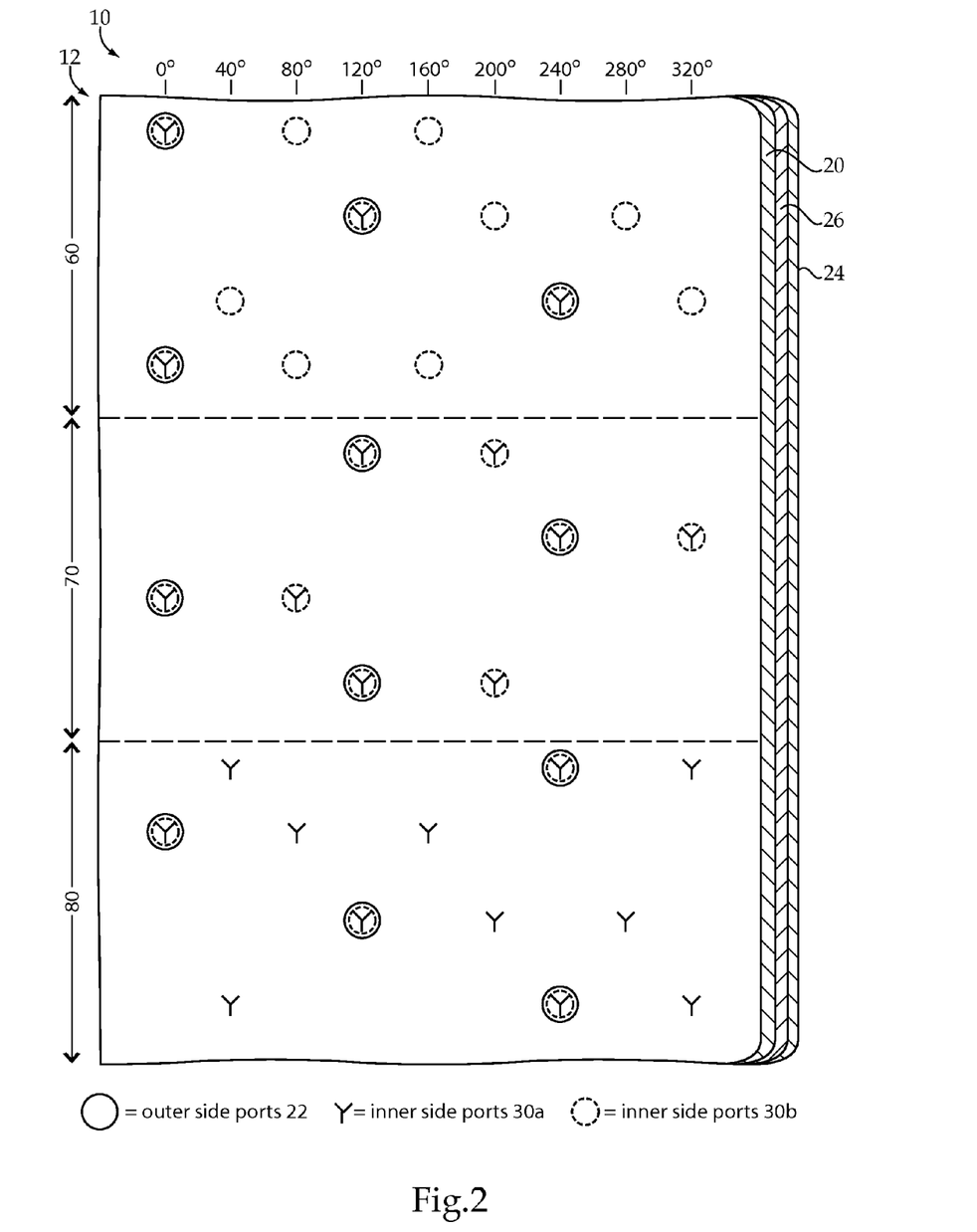
FIG. 2 is a diagrammatic view of a portion of the catheter of FIG. 1, cut lengthwise and flattened out to illustrate positions of side ports in a first configuration of the catheter.

Referring also now to FIG. 2, there is shown catheter 10 as it might appear where cut longitudinally and spread flat such that each of outer tube 20 and inner tubes 24 and 26 are more or less coplanar. In FIG. 2, solid circles designate outer side ports 22, whereas broken line circles designate inner side ports 30b, and the Y-shaped features designate inner side ports 30a. As noted above, inner side ports 30a may be normally closed, and are shown having a Y-shape to illustrate one normally closed port style having three convergent valve leaves, although slits or the like might also be used, or side parts 30a might instead be normally open. In FIG. 2, catheter 10, and more particularly tube assembly 12, is illustrated divided into a proximal section 60, a middle section 70, and a distal section 80, which will be understood to also designate corresponding proximal, middle, and distal sections of each of tubes 20, 24 and 26.

It will be recalled that catheter 10 may have as many as six different available infusion lengths, or possibly even more. To this end, catheter 10 may be placed in a plurality of different rotational configurations of tube assembly 12, each of which radially aligns outer side ports 22 with inner side ports 30a and 30b in a different way, and imparts a correspondingly different infusion length. Thus, catheter 10 may infuse liquid from only those outer side ports 22 which are in proximal section 60, only those outer side ports 22 which are in middle section 70, only those outer side ports which are in distal section 80, or any combination of sections 60, 70 and 80. In FIG. 2, all of outer side ports 22 are radially aligned with one of inner side ports 30b and one of inner side ports 30a such that catheter 10 has a full infusion length. Adjusting catheter 10 to a different rotational configuration may be visualized by sliding inner tube 24, inner tube 26, or both, left or right relative to outer tube 20 in FIG. 2, to result in a different combination of radial alignment among the various side ports.

Figure 3:
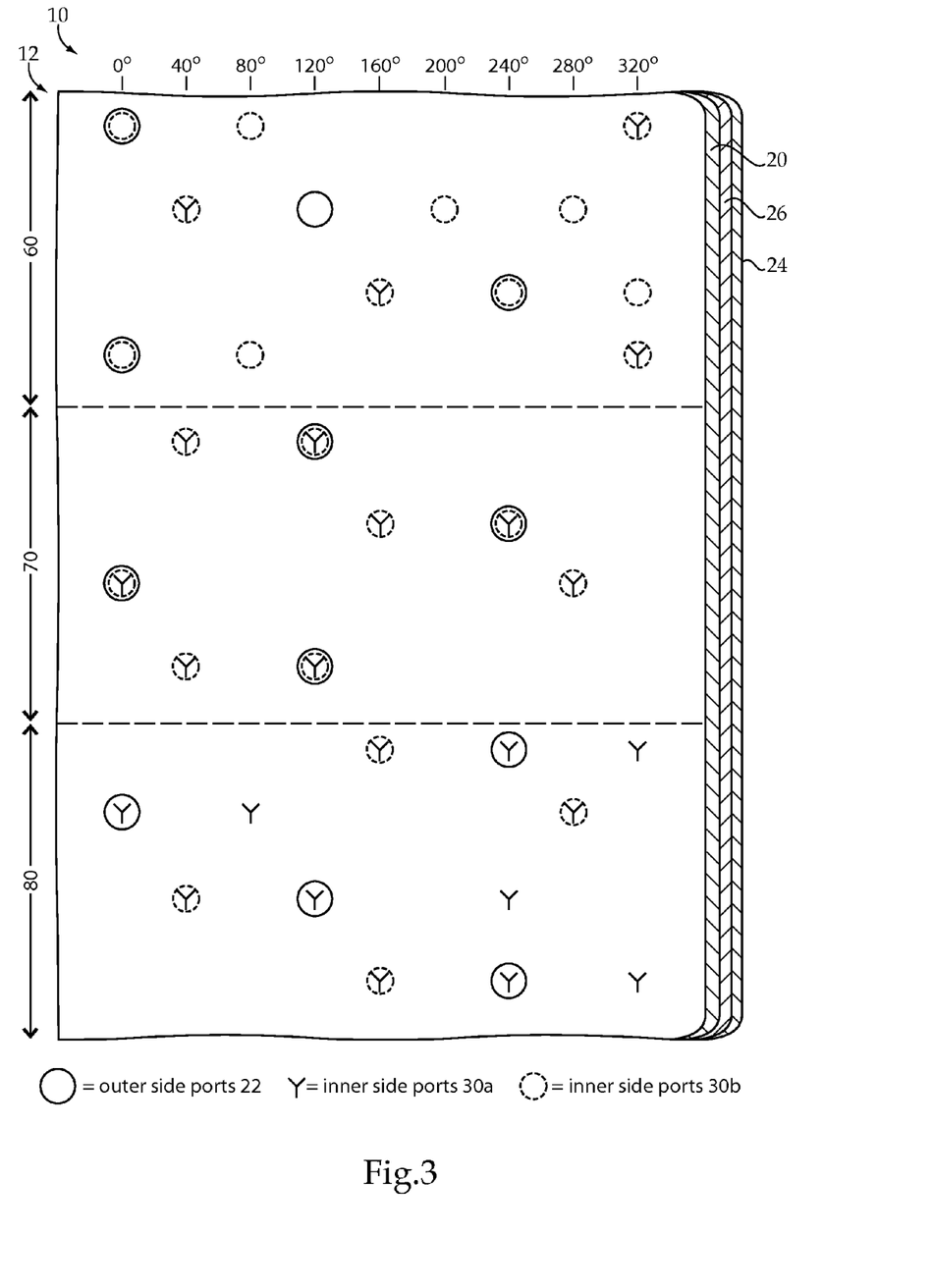
FIG. 3 is a view similar to FIG. 2, illustrating positions of the side ports in a second configuration of the catheter.

Referring also now to FIG. 3, there is shown catheter 10 and tube assembly 12 adjusted to another rotational configuration where only those outer side ports 22 which are in middle section 70 are radially aligned with both an inner side port 30a and an inner side port 30b, such that catheter 10 has a partial infusion length, namely, a middle infusion length. Thus, in FIG. 2 only the middle group of four outer side ports 20 within middle section 70 are in fluid communication with supply passage 28. In FIGS. 2 and 3, different angular orientations are shown illustrating approximate locations of side ports 22, 30a and 30b about 360°. Outer side ports 22 are shown spiraling about outer tube 20 at intervals of approximately 120°. Some of inner side ports 30a may be located approximately every 120°, as is the case with inner side ports 30b. Additional ones of inner side ports 30a and 30b may be offset from the 120° locations, as shown. In the illustrated embodiment, inner tube 26 has additional inner side ports 30b offset at 80° and 160° from the inner side ports 30b matching the locations of outer side ports 22 within proximal section 60, additional side ports offset 80° within middle section 70, and no additional inner side ports 30b within distal section 80. Inner tube 24 includes additional inner side ports 30a having a similar offset pattern to that of side ports 30a, but reversed as shown in FIG. 2.

It may thus be noted from FIGS. 2 and 3 that each of first inner tube 24 and second inner tube 26 has three different angular orientations relative to outer tube 20 at which radial alignment of some of their inner side ports with outer side ports 22 occurs. It may also be noted from FIGS. 2 and 3 that outer side ports 22 are shown slightly larger than inner side ports 30b, which in turn may be slightly larger than inner side ports 30a. The different sizing allows for some tolerance in misalignment. In certain embodiments, tubes 24 and 26 may be expected to twist slightly during rotation, and the outer side ports 22 in distal section 80, and possibly also in sections 60 and 70, might be made relatively larger than more proximal outer side ports 22 to compensate for the twisting. In a similar vein, inner tube 24, and also potentially inner tube 26 might be formed from material relatively stiffer than material of which outer tube 20 is formed to lessen the tendency to twist. Each of tubes 20, 24 and 26, may be formed from nylon or another suitable, typically extrudable, polymeric material, having different chemical formulations, additives, or geometric properties, to vary the stiffnesses in a known manner if desired.

In a practical implementation strategy, each of proximal section 60, middle section 70 and distal section 80 may be approximately 15 cm in length. The angular orientations of the various side ports, as well as the lengths of the different sections of catheter 10 might be varied from the embodiments shown without departing from the scope of the present disclosure. For instance, where a greater number of outer side ports is desired, outer side ports 22 might be relatively closer together both circumferentially and axially than what is illustrated in the attached drawings. Corresponding changes in the position and numbers of inner side ports 30a and 30b might then be made. In still other embodiments, a number of coaxial tubes in tube assembly 12 might be different from three. For instance, a total of two coaxial tubes might be used, having inner and outer side ports with different numbers and locations than those discussed and illustrated herein to impart a plurality of different available infusion lengths. Similarly, four coaxial tubes might be used in alternative embodiments. Markings may be provided on tubes 20, 24, and 26, near handles 34 and 32, to enable a clinician to determine a present rotational configuration of tube assembly 12, and thus a present catheter infusion length, as well as for adjusting the same.

Figure 4:
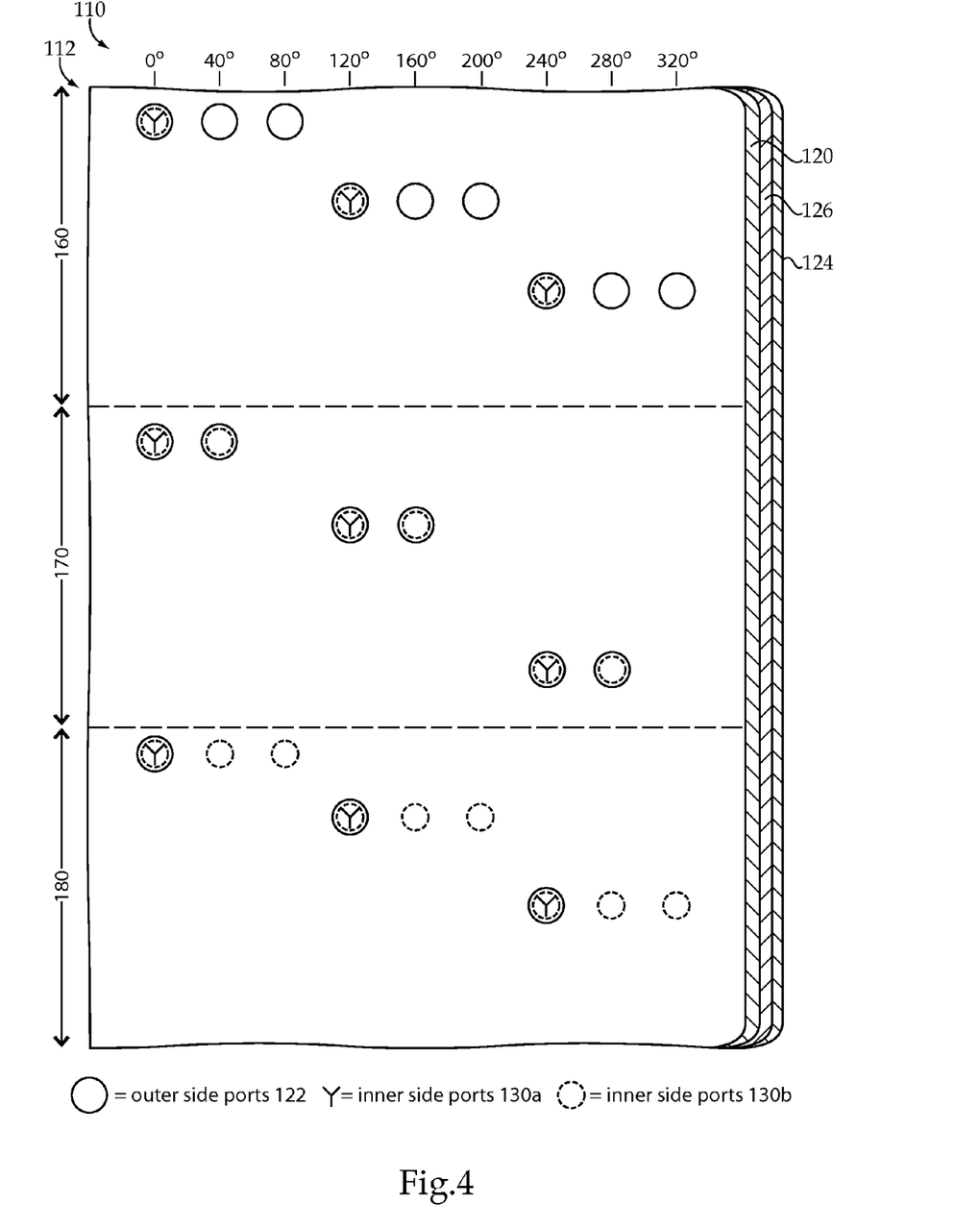
FIG. 4 is a diagrammatic view of a portion of a catheter according to another embodiment, and illustrated analogously to FIG. 2.

Referring now to FIG. 4, there is shown a catheter 110 having a tube assembly 112 according to another embodiment. Catheter 110 has certain similarities with the previously described embodiment, but a number of differences. Tube assembly 112 includes an outer tube 120, a first inner tube 124 and a second inner tube 126. A plurality of outer side ports 122 are formed in outer tube 120, a plurality of inner side ports 130a are formed in inner tube 124, and another plurality of inner side ports 130b are formed in second inner tube 126. Rotating one or more of tubes 120, 124 and 126 relative to the other tubes provides for different radial alignments among the various side ports, and corresponding different patterns of fluid communication with a fluid supply passage configured similarly to supply passage 28 of catheter 10, and imparts correspondingly different infusion lengths. Tube assembly 112 includes a proximal section 160, and distal section 180, and a middle section 170. Catheter 110 differs from the foregoing embodiment with regard to the arrangements of the various side ports, and their relative numbers within the corresponding tubes. In catheter 110, a number of inner side ports 130b in inner tube 126 may be equal to a number of outer side ports 122, in contrast to the foregoing embodiment in which equal numbers of inner side ports are formed in each of the first and second inner tubes, and a lesser number formed in the outer tube. Inner side ports 130b and outer side ports 122 may define opposite density gradients in an axial direction, again contrasting with the foregoing embodiment where an opposite density gradient of the corresponding side ports is defined by the two inner tubes and not the outer tube Inner side ports 130b and outer side ports 122 may have an equal density in a middle one-third of the corresponding tube 126 and 120. Inner side ports 130a may have a uniform density in an axial direction, and are arranged in a spiral pattern. The relative and absolute dimensions of tubes 120, 124 and 126, as well as tube assembly 112 itself, may in a practical implementation strategy be the same as or similar to the corresponding dimensions described in connection with catheter 10 above.

Catheter 110 may function analogously to catheter 10 as discussed elsewhere herein, and thus that description should be understood to analogously refer to catheter 110 except where otherwise indicated. Outer side ports 122 may be spaced apart at locations approximately every 120° around the circumference of tube assembly 112, at additional 40° and 80° offset locations in proximal section 160, at additional 40° offset locations in middle section 70, and having no outer side ports apart from the ones at the 120° locations in distal section 180. Inner side ports 130b may be located approximately every 120° around the circumference of tube assembly 112, at additional 40° and 80° offset locations within distal section 180, and at additional 40° offset locations in middle section 170, and with no additional offset locations in proximal section 160. From the state depicted in FIG. 4, one or more of tubes 120, 124 and 126 may be rotated to attain different infusion lengths of catheter 110. For example, second inner tube 126 might be rotated approximately 40° relative to the other two tubes to shut off flow from proximal section 160. Rotating second inner tube 126 another 40° in the same direction would shut off flow also from middle section 170, such that infusion flow occurs only through distal section 180. Rotating outer tube 120 40° from the configuration shown in FIG. 4 shuts off flow from distal section 180, and rotating outer tube 120 another 40° shuts off flow from middle section 170, such that only proximal section 160 infuses liquid. Rotating both outer tube 120 and second inner tube 126 40° relative to first inner tube 124 from the state shown in FIG. 4 results in flow only from middle section 170.

INDUSTRIAL APPLICABILITY

Figure 5:
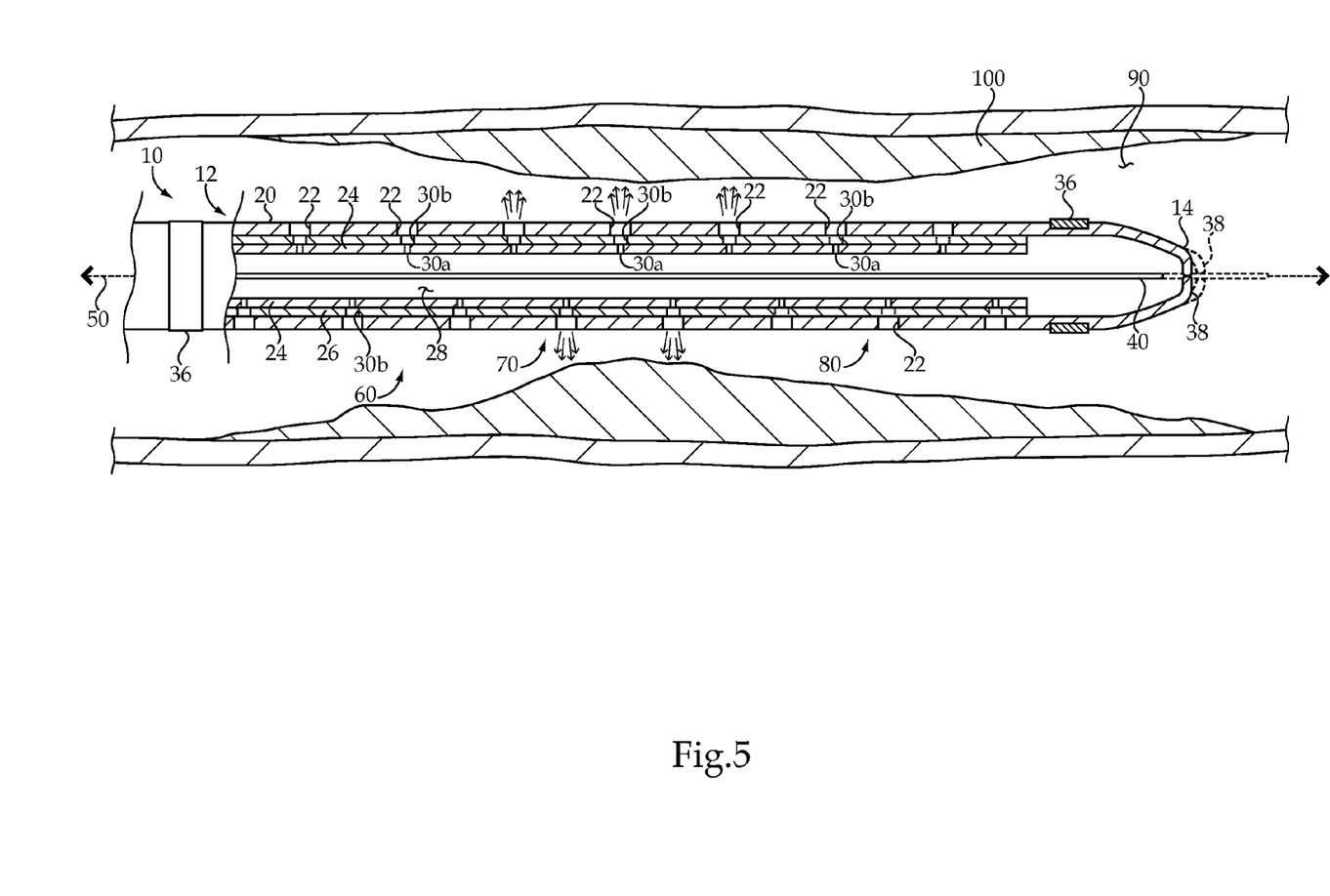
FIG. 5 is a sectioned side diagrammatic view of a portion of the catheter of FIG. 1 as it might appear at one stage of a treatment procedure, according to one embodiment.

Referring now to FIG. 5, there is shown catheter 10 as it might appear having been slid over a wire guide 40 through a percutaneous entry point in a patient's skin to a position within a body lumen 90 of the patient such as a vein or artery. Catheter 10 is shown extending through a lesion 100 such as a thrombus. Additional features of catheter 10 depicted in FIG. 4 include a set of radiopaque markers 36 which can enable a clinician to visually determine a location of catheter 10 within body lumen 90 via the assistance of radiography in a conventional manner. In the embodiment shown, catheter 10 includes a valved tip having a valve 38 positioned at distal end 40. Wire guide 40 has been retracted, moved left relative to catheter 10 in the FIG. 5 illustration, such that valve 38 has assumed a closed state blocking supply passage 38. Valve 38 may have an open state, assumed when wire guide 40 is positioned therein, and shown in phantom in FIG. 5. It will be recalled that inner side ports 30a may be normally closed, meaning that some fluid pressure is required to urge side ports 30a to a fully open position. Valve 38 may define a greater valve opening pressure, and each of inner side ports 30a may define a lesser valve opening pressure. In this way, as liquid is conveyed through passage 28 and infused into body lumen 90, the greater valve opening pressure of valve 38 can ensure that side ports 30a may be opened to infuse the liquid without opening valve 38. Instead of a valved tip, in alternative embodiments catheter 10 might include a passage formed in distal end 14 which extends through a part of catheter 10 without communicating with passage 28, such that wire guide 40 need not pass through passage 28 during introducing and guiding catheter 10 within a body lumen.

With catheter 10 positioned approximately as shown in FIG. 5, liquid may be conveyed from an extraluminal liquid supply through inlet orifice 18 and into passage 28, and thenceforth from inner side ports 30a to inner side ports 30b, and then to outer side ports 22 for infusing from body lumen 90. At the example stage of the treatment procedure depicted in FIG. 5, only a middle group of outer side ports 22 are in fluid communication with passage 28. A proximal group of outer side ports 28 are in fluid communication with inner side ports 30b, but are blocked from fluid communication with passage 28 via inner tube 24. A distal group of outer side ports 28 are blocked from fluid communication with inner side ports 30a, and thus passage 28, via inner tube 26. When and if it becomes desirable to adjust an infusion length of catheter 10, one or both of inner tubes 24 and 26 may be rotated relative to outer tube 20 to change the pattern of fluid communication among outer side ports 22 and inner side ports 30a and 30b. From the stage depicted in FIG. 5, one or both of inner tubes 24 and 26 might be rotated to block some of outer side ports 22 whilst opening, or maintaining open, others of outer side ports 22. For instance, additional outer side ports 22 may be opened, that is, placed in fluid communication with passage 28, such that an adjusted infusion length is an increased infusion length of catheter 10. Alternatively, rotating one or both of tubes 24 and 26 can decrease an infusion length of catheter 10 by blocking some outer side ports 22. For instance, if catheter 10 were in a state where it has a full infusion length and all of outer side ports 22 are infusing the liquid, one or both of tubes 24 and 26 might be rotated to block some of the outer side ports 22, and thus decrease the infusion length. A clinician might adjust an infusion length of catheter 10 multiple times during a percutaneous treatment procedure, for instance treating only the thickest part of a thrombus first, and then opening additional outer side ports to treat other parts of the thrombus once the thickest part has begun to dissolve. In the example shown in FIG. 4, a clinician could well be infusing liquid towards lesion 100 from only middle section 70, and then could open additional outer side ports from at least one of proximal section 60 and distal section 80 to treat the rest of lesion 100. All of these adjustments to infusion length may take place without changing a position of catheter 10 within body lumen 90. Catheter 110 will function generally analogous to catheter 10, and the foregoing description should thus be considered to analogously refer thereto.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A variable infusion length catheter comprising:
    a tube assembly including a distal end positionable within a body lumen in a patient, and a proximal end having a fitting with an inlet orifice formed therein, for fluidly connecting with a supply of liquid;
    the tube assembly further including an outer tube defining a longitudinal axis and having formed therein a plurality of axially spaced outer side ports, for infusing the liquid into the body lumen;
    the tube assembly further including at least one inner tube positioned coaxially within the outer tube, and having formed therein a supply passage configured to receive the liquid from the inlet orifice, and a plurality of axially spaced inner side ports configured to convey the liquid from the supply passage to the outer side ports;
    the outer tube being in contact with an adjacent one of the at least one inner tube along a segment of the tube assembly that includes the inner side ports and the outer side ports; and
    the at least one inner tube being rotatable within the outer tube to change a pattern of fluid communication among the outer and inner side ports and responsively adjust the infusion length of the catheter.

2. The catheter of claim 1 wherein the inner and outer side ports have at least three different combinations of radial alignment defining at least three patterns of the fluid communication, such that the catheter has at least three different available infusion lengths.

3. The catheter of claim 2 wherein the at least three infusion lengths include a middle infusion length where only a middle group of the outer side ports are in radial alignment with the inner side ports to receive the liquid conveyed from the supply passage.

4. The catheter of claim 2 wherein the at least one inner tube includes a first inner tube having the supply passage formed therein, and a second inner tube positioned radially between the first inner tube and the outer tube.

5. The catheter of claim 4 wherein a number of the inner side ports in the second inner tube is equal to a number of the outer side ports.

6. The catheter of claim 5 wherein the inner side ports in the second inner tube and the outer side ports define opposite density gradients in an axial direction.

7. The catheter of claim 6 wherein the inner side ports in the second inner tube and the outer side ports have an equal density in a middle one-third of the corresponding tube.

8. The catheter of claim 4 wherein the inner side ports in the first inner tube have a uniform density in an axial direction, and are arranged in a spiral pattern.

9. The catheter of claim 4 wherein the inner side ports formed in the first inner tube are normally closed, and the inner side ports formed in the second inner tube are normally open.

10. The catheter of claim 9 wherein the distal end of the tube assembly includes a valved tip having a closed state blocking the supply passage, and an open state, and wherein the valved tip defines a greater valve opening pressure and each of the normally closed inner side ports defines a lesser valve opening pressure.

11. The catheter of claim 4 wherein each of the combinations of radial alignment corresponds to a different combination of angular orientations of both the first and second inner tubes relative to the outer tube, about the longitudinal axis.

12. A method of percutaneously treating a patient comprising the steps of:
conveying a liquid from a plurality of inner side ports formed in an inner tube of a coaxial tube assembly in an infusion catheter to a plurality of outer side ports formed in an outer tube of the coaxial tube assembly;
infusing the liquid from the outer side ports into a body lumen of the patient;
rotating the inner tube to change a pattern of fluid communication among the outer and inner side ports which defines an infusion length of the infusion catheter; and
infusing additional liquid into the body lumen at an adjusted infusion length defined by the changed pattern of fluid communication due to the outer tube being in contact with the inner tube along a segment of the coaxial tube assembly that includes the inner side ports and the outer side ports.

13. The method of claim 12 further comprising a step of rotating a second inner tube located radially between the first inner tube and the outer tube and having another plurality of inner side ports formed therein, such that the changed pattern of fluid communication results from a changed radial alignment among the inner side ports formed in each of the first and second inner tubes.

14. The method of claim 12 further comprising a step of blocking some of the outer side ports via the rotating step such that the adjusted infusion length is a decreased infusion length of the infusion catheter.

15. The method of claim 12 further comprising a step of opening additional outer side ports via the rotating step such that the adjusted infusion length is an increased infusion length of the infusion catheter.

16. The method of claim 12 wherein the body lumen is a vascular lumen, and wherein the first infusing step includes infusing the liquid from only a middle section of the infusion catheter, and the second infusing step includes infusing the additional liquid without repositioning the infusion catheter within the vascular lumen.

17. The method of claim 12 wherein the second infusing step includes infusing the additional liquid from the middle section and also from at least one of a proximal section and a distal section of the infusion catheter.

18. A tube assembly for an infusion catheter comprising:
an outer tube defining a longitudinal axis and having formed therein a plurality of axially spaced outer side ports, for infusing a liquid into a body lumen of a patient;
at least one inner tube positioned coaxially within the outer tube, and having formed therein a supply passage configured to receive the liquid from an inlet orifice of the infusion catheter, and a plurality of axially spaced inner side ports configured to fluidly connect the outer side ports with the supply passage;
the at least one inner tube being rotatable within the outer tube to adjust the tube assembly from a first rotational configuration where only some of the outer side ports are in fluid communication with the supply passage and the catheter has a partial infusion length, to a second rotational configuration where all of the outer side ports are in fluid communication with the supply passage and the catheter has a full infusion length; and
the outer tube being in contact with an adjacent one of the at least one inner tube along a segment of the tube assembly that includes the inner side ports and the outer side ports.

19. The tube assembly of claim 18 wherein only a middle group of the outer side ports are in fluid communication with the supply passage in the first rotational configuration.

20. The tube assembly of claim 18 wherein the at least one inner tube includes a first inner tube, and a second inner tube located radially between the first inner tube and the outer tube.

* * * * *